United States Patent [19]

Thompson

[11] Patent Number: 4,594,069
[45] Date of Patent: Jun. 10, 1986

[54] DENTAL CROWN REMOVER

[76] Inventor: Benedict D. Thompson, 9008 Grape Creek Rd., Walkersville, Md. 21793

[21] Appl. No.: 658,527

[22] Filed: Oct. 9, 1984

[51] Int. Cl.⁴ ............................................. A61C 3/00
[52] U.S. Cl. .................................... 433/157; 433/158; 433/161; 433/162
[58] Field of Search ............... 433/161, 162, 157, 158, 433/153, 144, 218

[56] References Cited

U.S. PATENT DOCUMENTS

| | | | |
|---|---|---|---|
| 1,109,096 | 9/1914 | West | 433/161 |
| 1,176,548 | 3/1916 | Harpin | 433/144 |
| 1,858,081 | 5/1932 | Flagstad et al. | 433/161 |
| 2,428,689 | 10/1947 | Sykes | 433/157 |
| 3,690,007 | 9/1972 | Curtis | 433/158 |
| 4,196,520 | 4/1980 | Hoffman | 433/153 |

FOREIGN PATENT DOCUMENTS 435004  9/1935  United Kingdom ............... 433/161

Primary Examiner—John J. Wilson

[57] ABSTRACT

A dental crown (cap) remover with unique crown separating and removing means is adaptable to a wide variety of crown sizes and configurations and does not place compressive or axial forces on the underlying tooth or its supporting processes (alvoelar bone and periodontal fibers). The crown remover has a grasping and tightening mechanism that allows the dentist operator to firmly seat the crown remover on the crown to be removed, and has an elliptical separating mechanism that inserts in a precut groove in the crown and forces separation of the halves of the crown, increasing the circumferential dimension breaking the cementing medium and loosening the crown from the underlying tooth, providing for ease of separation of the crown from the tooth.

9 Claims, 8 Drawing Figures

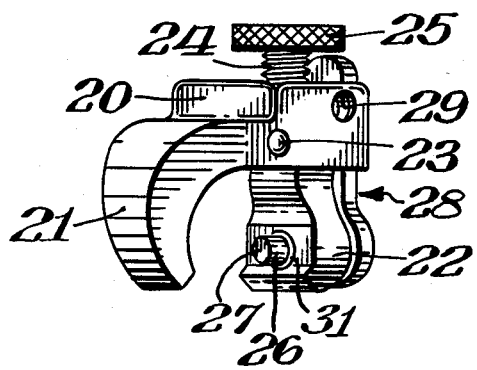
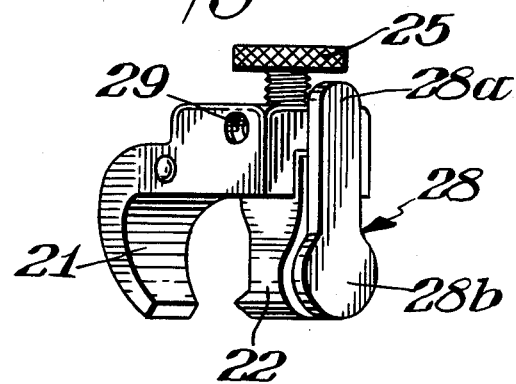
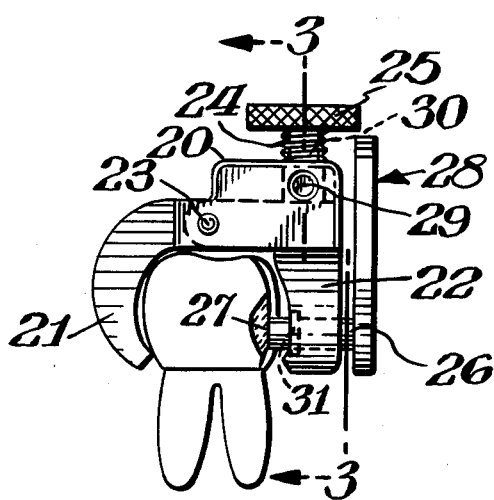
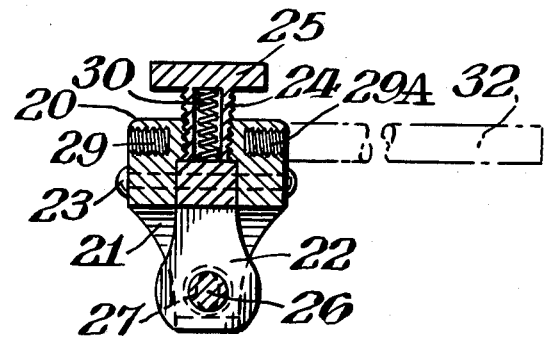
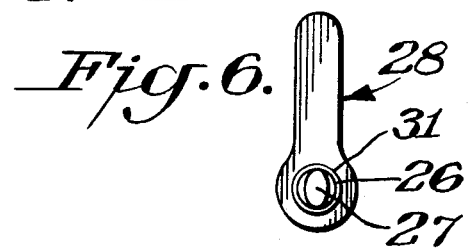
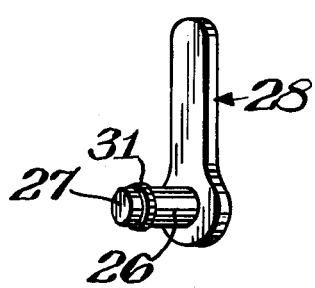
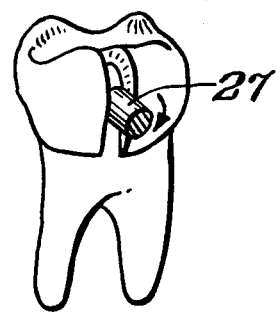

DENTAL CROWN REMOVER

BACKGROUND OF THE INVENTION

This invention relates in general to dental appliances and in particular to devices used to remove fabricated crowns from teeth restored in such a manner. The fabricated crown, usually of precious metal, porcelain, or a combination, has proven to be a very functional and durable dental restoration, and is intended to be permanently affixed to the underlying tooth. On many occasions, however, it is necessary for the dentist to remove the crown to provide further and more comprehensive treatment, to treat conditions that may arise, or for a variety of reasons. More often than not, it is desirable to remove the crown in such a way that the underlying tooth and its supporting mechanism will remain intact, and will not be harmed or compromised in any way.

A variety of devices have been patented for the purpose of removing crowns from teeth, yet these devices have not received widespread use in the dental profession as the existing devices generally depend to a large extent on the optimum integrity of the underlying tooth structure and the supporting processes. Very often the dentist cannot determine the integrity of the underlying tooth structure and correctly supposes he could damage tooth through use of an existing crown remover. A widespread technique of dentists is, when the integrity of the tooth is in question, to slice the crown in such a manner that it may be easily removed.

Kenney U.S. Pat. No. 989,267 discloses one of the earlier practical devices for the removal of crowns, and proposed removal of the crown without damage to the crown or the natural tooth structure. His invention was comprised of a set of arms that firmly grasped the crown in an unyielding manner and a threaded member that passed through an opening cut in the crown and seated on the underlying natural tooth structure. As the threaded member was turned, a force was applied to the tooth structure, and an equal and opposite force lifted the crown from the tooth. Subsequently Kennedy U.S. Pat. No. 1,041,098, West U.S. Pat. No. 1,109,096, Flagstad U.S. Pat. No. 1,858,081, Wilson U.S. Pat. No. 3,755,901, and Zatkin U.S. Pat. No. 3,889,376 all provide some improvement of the basic mechanism, but each inventor supposes that the underlying tooth is sufficiently strong to resist the forces necessary to dislodge the crown. This method places little stress on the tooth supporting processes, and the likelihood of an inadvertent extraction is remote, but if the underlying tooth structure is weak, if it has been built up through the use of core materials and retention pins, or if it consists of crown cementing medium, the probability of fracturing the core material, dislodging the pins, fracturing the natural tooth material, and causing irreversible damage to the underlying tooth is extremely likely.

Johnson U.S. Pat. No. 1,177,706 addressed this problem by patenting a device which forced inclined members between the crown and the natural tooth at the gingival margin. The use of his device assumed the presence of a 1 millimeter or so horizontal shoulder at the gingival margin—an assumption that is not valid by current concepts of the practice of restorative dentistry.

This same problem was addressed by Curtis U.S. Pat. No. 3,690,007 directed to a device that also embraced in an unyielding manner the crown to be removed and providing an eyelet that the operator could insert a hook or "back action hammer" that would provide a constant or intermittent force in an axial direction away from the crown. The use of such device assumes that the force can be adequately applied in an axial direction (this may prove difficult in the posterior teeth) and that the tooth supporting processes are of adequate strength to resist the force necessary to separate the crown from the tooth. The principle of operation of such device is remarkably similar to devices patented by Maranda U.S. Pat. No. 1,666,860 and Lococo U.S. Pat. No. 4,230,454 for the extraction of teeth in that it has the potential of applying enough force to cause inadvertent extraction of the underlying tooth.

All of the above listed crown removers provide a mechanical means and in most cases a mechanical advantage for removing crowns from teeth. All the devices operate by applying a force to the underlying tooth structure or in the case of Curtis U.S. Pat. No. 3,690,007 applying a force to the tooth support processes. All these methods of operation assume the underlying structures can safely tolerate these forces, and in the case of Johnson U.S. Pat. No. 1,177,706 the underlying tooth was prepared in a specific manner.

A prior art publication which teaches use of a prying action to spread the crown apart and expand the crown circumferentially is Hoffman U.S. Pat. No. 4,196,520. However, this device is not seated on the crown in such a manner that would ensure firm and proper engagement of the crown expanding means, nor does it provide a force multiplying means.

SUMMARY OF THE INVENTION

A dental crown remover is disclosed which comprises two arms extending and pivoting from an axis with the arms formed to firmly engage a dental crown and a crown separating means attached to one of said arms whereby the separating means provides an outward force toward the circumference of the crown without substantially any compressive force.

In a preferred embodiment the crown separating means includes an elliptical cam which provides a force multiplying means to facilitate separation of the crown.

OBJECTS OF THE INVENTION

An object of the present invention is to provide an acceptable and practical means of safely removing a crown from the underlying tooth without causing damage to said tooth or its supporting processes.

A further object is to remove the crown in such a manner as to render it suitable to be reused as a temporary restorative medium.

Still a further object is to provide a device that is effective, yet is simple to use and economical to manufacture.

The present invention is of practical use because it eliminates some of the problems associated with previous crown removers. It is universal in application in that it can be used on both anterior and posterior crowns and it is adaptable to a wide variety of crown sizes and configurations. Most crowns can be removed with a high degree of safety without undue stress placed on the underlying tooth or its supporting processes.

BRIEF DESCRIPTION OF THE DRAWINGS

FIG. 1A is a perspective view of the crown remover according to a typical embodiment of the present invention FIG. 1B is another perspective view of the crown remover of FIG. 1A, as seen from another direction FIG. 2 is an elevation view of the crown remover, seated in position to remove crown FIG. 3 depicts the crown remover as seen through A—A' of FIG. 2

FIG. 4 illustrates detail of the crown separating means

FIG. 5 depicts an accompanying handle

FIG. 6 is another view of the crown separating means of FIG. 4

FIG. 7 depicts the terminal portion of a rotatable member inserted into a channel in the crown.

DETAILED DESCRIPTION OF THE INVENTION

For purposes of promoting an understanding of the principles of the invention, reference will now be made to the embodiment and components illustrated in the drawings and specific language will be used to describe the same. It will nevertheless be understood that no limitation of the scope of the invention is thereby intended, such further modifications and alterations of the illustrated device and such further applications of the principles of the invention as illustrated therein being contemplated as would normally occur to one skilled in the art to which the invention relates.

With reference to FIG. 1A, there is illustrated a crown removing device 20 which includes arms 21 and 22 which extend from and pivot about pin 23 and are shaped in such a manner to firmly embrace a dental crown. An extended portion of arm 21 contains a threaded member through which activating screw 24 is threaded. To one end of screw 24 is fixed knob 25 by which said screw is manipulated. The opposite end of said screw rests on a seat of arm 22, which seat is a distance removed from the pivot pin 23. Housed in arm 22 is the crown separating means which comprises an elongated member which has a cylindrical portion 26 that rotates freely in arm 22, and that portion of the elongated member which extends from the inner surface of arm 22 and facing the crown terminates in a non cylindrical, preferably elliptical, shape 27, while the opposite end is affixed to a rotatable member 28. Arms 21 and 22 are held in a generally closed or seated position by a spring mechanism housed in screw 24 and is seated on arm 22 in a manner congruent with screw 24. On either side of the embodiment 20 a threaded recess is provided for the attachment of a removable handle.

A more complete illustration of the position of the elongated member with its cylindrical portion 26 and elliptical end 27, and the rotatable member 28 is presented in FIG. 2. The position of activating screw 24 in the threaded extension of arm 21 and the position of internal spring mechanism 30 housed in said activating screw is also seen here.

Another illustration of the position of the activating screw in the threaded extension of arm 21 and the internal spring mechanism is shown in FIG. 3. Threaded recesses 29 and 29A are shown on either side of the embodiment 20. FIG. 4 depicts a typical configuration of the cylindrical portion 26, its termination into an elliptical shape 27, and the attachment into rotatable member 28. Retaining member 31 is permanently affixed over the elliptical end of cylindrical portion 26 at some distance from said end, and said retaining member freely rotates within a recess in the inner surface of arm 22 concentric with cylindrical member 26. FIG. 6 is another view of the FIG. 4 embodiment of the crown separating means.

An auxiliary handle 32, shown in FIG. 5, terminates in a threaded portion that allows temporary and removable fixation of said handle to the embodiment 20 at threaded portions 29 and 29A.

Prior to operation of the dental crown remover, it is ordinarily necessary to form a channel, i.e., a precut groove within one exposed wall of the crown and extending through the thickness of the wall. The crown remover is seated in such a way on the crown that arm 21 grips an outer surface of the crown and arm 22 is placed over the surface with the precut channel so that elliptical end 27 is extended within the channel. The width of the channel in the crown allows the elliptical end 27 to be inserted into the channel with the narrow portion of such end 27 facing the walls of the channel. The end 27 would not otherwise fit into the channel. FIG. 7 shows the elliptical end 27 only within the channel walls with the major axis of the ellipse extending lengthwise in the channel with the minor axis bridging the channel wall prior to rotation. Tightening of knob 25 causes arm 21 and arm 22 to firmly seat and hold elliptical member 27 in the precut channel. Thereafter by rotation of the rotatable member 28 at its end 28a a force multiplication is realized with force applied to the end 28b. Elliptical end 27 then rotates which by applying force toward the circumference of the crown causes an enlargement of the circumference, breaking the cementing medium, allowing the crown to separate from the underlying tooth, without substantially any compressive forces being applied to the tooth or its supporting structures.

Additionally in accordance with the disclosed crown remover, its operation can be in a manner that little or substantially no axial force is applied to the tooth. Axial in the present context means a lengthwise tooth direction from the root structure to the end portion of tooth normally contacting the crown.

The present apparatus causes the crown to expand, i.e., enlarge, circumferentially. However, unlike Hoffman U.S. Pat. No. 4,196,520 the present application allows the crown remover to seat on the crown prior to use.

It is to be understood that though a dental crown removing device has been illustrated and described, various features of the invention will undoubtedly have other applications. The optimum materials and dimensions will depend largely on the intended application of the device. The invention has been described and illustrated in the drawings and the foregoing description, and this is intended to be illustrative and descriptive in nature, and in no way restrictive, it being understood that only the preferred embodiment and components have been shown and described, and that all changes and modifications that come within the spirit of the invention are desired to be protected. Illustratively, end 27 has been referred to as elliptical but it can have a non-cylindrical configuration.

What is claimed is:

1. A dental crown remover comprising two arms extending and pivoting from an axis, said arms having means for firmly engaging a dental crown and having crown separating means rotatably attached to one of said arms for providing an outward force toward the circumference of the crown without substantially any compressive force wherein said rotatable separating means includes an elongated member for applying said outward force to the crown by rotation of said separating means, whereby upon rotation of said separating means said outward circumferential force causes an enlargement of the circumference of said crown to allow the crown to separate from an underlying tooth.

2. The dental crown remover of claim 1 wherein said rotatable separating means has a non-cylindrical configuration adjacent the crown to facilitate the application of an outward force to the circumference of the crown.

3. The dental crown remover of claim 2 wherein said non-cylindrical configuration is at an end position.

4. The dental crown remover of claim 3 wherein said non-cylindrical configuration is elliptical.

5. The dental crown remover of claim 4 wherein said rotatable separating means has an extension which allows a force multiplication to be applied to said elongated member.

6. The dental crown remover of claim 1 wherein said rotatable separating means has an extension which, upon rotation, allows a force multiplication to be transferred along the circumference of the dental crown.

7. A dental crown remover of claim 1 wherein the means for firmly engaging a dental crown comprises a threaded member housed in an extension of one arm and engaging a second arm at a distance from the pivot axis with pressure activating means to hold said arms toward a generally closed position, said pressure activating means being housed within the threaded member.

8. The dental crown remover of claim 7 with adjustment means having a removable handle which can be attached in several positions.

9. A dental crown remover comprising two arms extending and pivoting from an axis with the arms formed to firmly engage a dental crown, a crown separating means attached to one of said arms whereby the separating means provides an outward force toward the circumference of the crown without substantially any compressive force, and means to adjust and firmly hold the arms in position on the crown comprising a threaded member housed in an extension of one arm and engaging a second arm at a distance from the pivot axis with pressure activating means to hold said arms toward a generally closed position, said pressure activating means being housed within the threaded member.

* * * * *